July 25, 1933. J. A. SIMPSON Plant Pat. 73

PECAN TREE

Filed Aug. 18, 1932

Inventor

James A. Simpson

By Watson E. Coleman.

Attorney

Patented July 25, 1933

Plant Pat. 73

UNITED STATES PATENT OFFICE

JAMES A. SIMPSON, OF UVALDE, TEXAS, ASSIGNOR TO HUMBLE OIL & REFINING COMPANY, OF HOUSTON, TEXAS, A CORPORATION OF TEXAS

PECAN TREE

Application filed August 18, 1932. Serial No. 629,350.

This invention relates to nut trees and particularly to a new and distinct variety of pecan. Being a horticulturist, making a specialty of pecans and frequently inspecting various groves, it happened that while inspecting a native grove on land owned by the Humble Oil and Refining Company, of Texas, I noticed a pecan tree which was at that time but a sapling, probably having the age of fifteen years. It was badly crowded by other trees and I was given permission to begin my experiments by removing the excess growth of pecan and other timber and foreign growths around it and cut the tree back in order to form a sturdier head.

In the summer of 1928, I set buds of this "Mother" tree after I had noted that this "Mother" tree had set the second successive heavy crop, a thing most unusual with native seedlings. These buds bloomed and fruited heavily, an unusual and most desirable trait in pecans. Having supervision of a pecan grove, I topped one of the most vigorous, but shy-bearing, trees in the winter of 1928 and 1929 and started a novel test tree by placing buds of practially all the present recognized best varieties upon it, among them being buds of this "Mother" tree above referred to. There were seventeen different varieties in all. The buds of the "Mother" tree bloomed and set and matured fruits in 1930, whereas none of the other varieties did so, although they were all placed upon the same tree at the same time and in the same manner.

Last season this was repeated, the buds from the "Mother" tree being very heavily loaded with fruit while none of the other varieties fruited. This "Mother" tree is still living and is fruiting heavily this season. This "Mother" tree is situated about two hundred yards south of the Uvalde County-Zavalla County line, and about one quarter mile from the bank of the Neuces River. Thus the location of this tree is in Zavalla County, Texas. I have asexually reproduced the variety by all of the commonly practiced methods of bud and graft insertions and have proved to my own satisfaction that it is a valuable addition to the list of varieties for the following reasons:—

It is the heaviest bearing variety that has ever come under my observation. It has fruited heavily each of the five years that it has been under my observation. The cluster formations of the nuts are as near to an ideal as are found anywhere, the nuts being openly spaced along a sturdy fruit petiole and each cluster containing upon an average of seven nuts. The nuts are large, averaging forty-five to fifty per pound. The nuts contain about fifty-five per cent of meats of particularly good flavor. The variety seems to be unusually free from troubles due to fungus growths such as scab, mildew, etc., and has never shown any trace of Rosette or Die-back even when placed upon trees badly affected by those troubles. The shape of the nuts is particularly good and the shell is of medium thickness and hardness. The variety is very easy to propagate having full, plump, well-developed and rounded buds and nearly always having three or four buds visible in the leaf axils.

The tree is heavily foliaged and a voracious feeder, and hence it fills its fruits uniformly well and brings a large percentage of fruits set to full maturity. The annexed drawing illustrates the particular characteristics of this variety of pecan.

The staminate male flowers of this variety of pecan grow upon very long and very numerous catkins six to eight inches in length.

The flowers are of relatively large or coarse type. The color of the entire catkins, stem, pollen sacs, etc., is a deep dark green, which color is retained up to and during dehiscence. The pistillate flowers of this variety do not differ greatly from the pistillate flowers of other varieties. Both male and female blooms appear exceptionally late in the season and the periods of dehiscency and receptivity of these flowers extend over a longer period than in the case of most varieties, thus insuring self-fertility and making of the variety a valuable pollen distributor for other sorts.

This variety of pecan blooms very late in Texas, the blooming period being from late May to mid-June. On the other hand, it matures earlier than any other variety known to me, usually by September 1st. The hulls of this variety of pecan are heavily ribbed and of a deep green color. The surfaces of the hulls are rough, thus being distinguished from many other varieties where the hulls are smooth and glossy. The kernels of the nuts are slightly wrinkled but the sutures are open and the kernels release cleanly from the shell. The flavor of the nuts is particularly good.

The buds are very short and full and stand out very prominently on the leaf axils and the latter, due to the heavy petiole that develops, are very heavy and robust. The leaf petiole is heavy and coarse and the leaves are large, very often being two feet in length. The trunk of this particularly variety of pecan is cylindrical and never flattened as is the case in several varieties of pecans, namely, the Burkett and Mahan varieties. The "nodes" of my new variety of pecan are straight and not sharply elbowed as in some varieties as, for instance, the "Sovereign" and "Squirrel's Delight". The new bark of a current season's growth is very smooth, thin and of a deep green hue, beautifully flecked with silver.

While the "Mother" tree of this variety is only about twelve to fifteen years of age and about six inches in diameter, so that it is not known how rough the bark may become, yet I believe the tree to be a smooth bark variety.

The most outstanding characteristic and desirable feature of the variety is that it bears its fruits upon a long sturdy fruit petiole with much space between the nutlets. This is a very valuable feature for several reasons: It secures greater immunity from insect ravages, permits free circulation of air and sunlight and permits the drainage therefrom of excessive moisture.

A further characteristic and most desirable feature is that the clusters of fruits usually contain from six to ten nuts and another characteristic is that fully fifty per cent of the buds set in summer budding operations, bear fruit and mature the fruits in from eleven to thirteen months.

The nut of my variety of pecan has the following outstanding characteristics:—The nuts will run approximately 45 to 50 nuts per lb., but may range above or below these figures according to the growing conditions. The average shape of the nuts varies slightly according to growing conditions and may be described as follows:—

*Apex.*—Of usual form found in pecans, gently pointed and somewhat flattened toward the plane of the kernel partition.

*Base.*—Not gently rounded as almost universal for pecan nuts but abruptly flattened.

*General shape, apex to base.*—Cylindrical to elliptical.

*Measurements.*—For nuts averaging 48 per pound the dimensions are approximately as follows:—Average length, tip of base to tip of apex, about 4.51 centimeters; average maximum thickness in plane of kernel partition, 2.33 centimeters; average maximum thickness at right angles to plane of kernel partition, 2.21 centimeters.

*Normal external shell color and markings of nuts.*—The normal background color of the shell is the usual light brown common to pecans, upon which are stripes and dots of dark purple to black color.

The pattern of the markings is as follows:—The apex of nut is well striped with irregular bands of dark purple to black color. The remaining surface of the nut not covered by bands is finely dotted all over.

*Normal thickness and character of shell.*—The normal thickness of shell ranges from 1.1 to 1.4 millimeters, an average being about 1.24 millimeters. The inside of the shell is lightly ruffled throughout, causing the kernel to be finely corrugated on the outer surface.

*Normal internal characteristics.*—The central partition septum is high but in well filled pecans is commonly more or less folded over against the partition so that it does not extend through the base of the kernel. Well developed ridges on the partition occur on each side of the central septum and run parallel to it. The kernel does not differ materially in color, flavor, and texture from that ordinarily found in pecan nuts. In form, it conforms to the peculiarities of the internal shell surface and the kernal partition against which surfaces it is molded.

I have heretofore referred to the fact that the nodes of my new variety of pecan are straight and not elbowed or curved. The stem of this new variety has straight nodes upon the bud wood and especially upon current growths. This is particularly advantageous in that where "bud sticks" are angled or curved, there is difficulty in so cutting the buds that the buds will fit upon the straight surfaces upon which propagators always try to place the buds. Unless the bud is cut from a relatively straight bud stick, the cambium layer of the bud will not come into exact and close contact with the cambium layer of the tree into which the bud is inserted.

It is seen, therefore, that I have discovered a variety of pecan that is a very late blooming variety and a very heavy blooming and bearing variety and that the fruits are borne upon a long and sturdy fruit petiole with the advantages heretofore stated.

It will further be seen that the fruit clusters usually contain from six to ten nuts or a larger number than are ordinarily borne by the fruit clusters of other varieties of pecans known to me.

Many clusters, I may state, have been observed last season which contain as high as twelve nuts.

In the drawing accompanying this application, Figure 1 is an enlarged view of a portion of a small branch of this new variety of pecan such as would be used with a bud stick showing the character of the petioles extending from the branch and of the buds carried at the leaf axils and also illustrating the general straightness of the current growth on the pecan;

I claim:—

Figure 3:
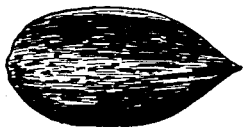
Figure 3 is a view of the nut itself.
Figure 4:
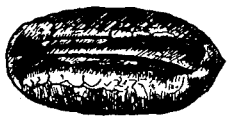
Figure 4 is a view of the kernel of the nut.
Figure 5:
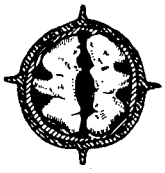
Figure 5 is a cross section through the nut and the rind or hull, showing the relatively heavy ribs on the hull.
Figure 2:
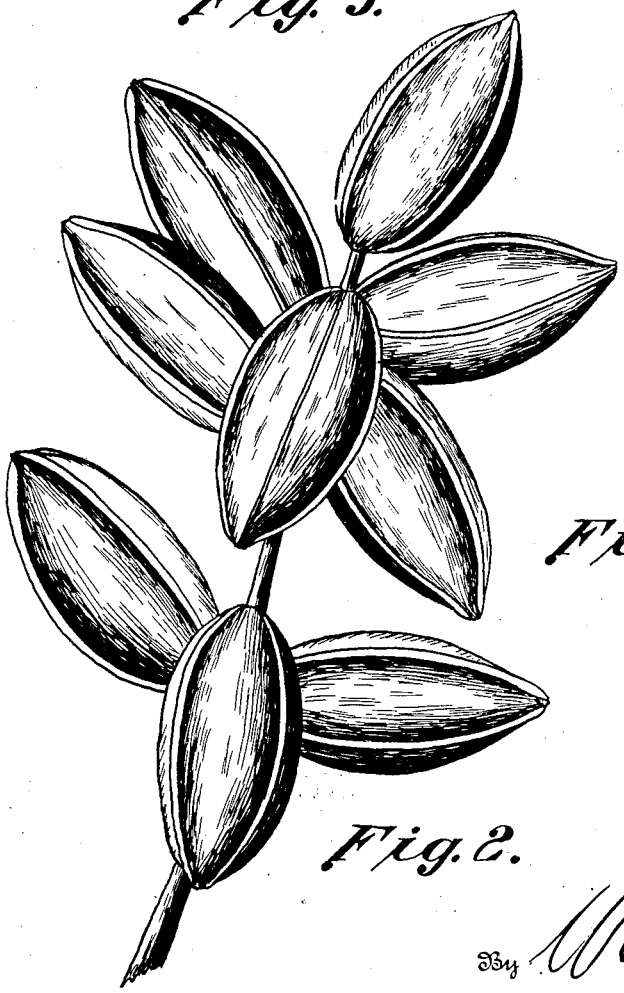
Figure 2 is a perspective view of a nut cluster of the pecan.
Figure 1:
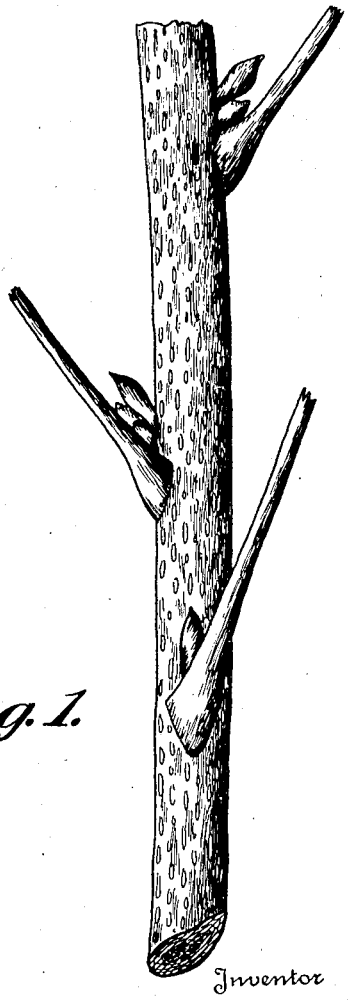

A pecan nut tree as described characterized by its vigorous growing habits, heavy fruitage, nuts being openly spaced and being large, in which both male and female blooms appear late in the season, and the periods of dehiscency and receptivity extend over a relatively long period having a relatively late blooming period but maturing early, the hulls of the nuts being heavily ribbed and the surfaces of the hulls being rough and the stems having straight nodes upon current growths.

JAMES A. SIMPSON.